United States Patent
von Daehne

[11] 3,954,735
[45] May 4, 1976

[54] DERIVATIVES OF α-AMINOBENZYLPENICILLIN

[75] Inventor: Welf von Daehne, Rungsted Kyst, Denmark

[73] Assignee: Lovens kemiske Fabrik Produktionsaktieselskab, Ballerup, Denmark

[22] Filed: June 7, 1971

[21] Appl. No.: 150,824

[30] Foreign Application Priority Data
June 17, 1970 United Kingdom............... 29467/70

[52] U.S. Cl............................. 260/239.1; 424/271
[51] Int. Cl.²..................................... C07D 499/44
[58] Field of Search.................................. 260/239.1

[56] References Cited
UNITED STATES PATENTS
3,198,804   8/1965   Johnson et al.................. 260/239.1
3,679,663   7/1972   Essery............................. 260/239.1

OTHER PUBLICATIONS
Daehne et al., Jour. of Med. Chem. Vol. 13, No. 4, pp. 607–612 (1970).

Primary Examiner—Nicholas S. Rizzo
Attorney, Agent, or Firm—Jackson, Jackson & Chovanes

[57] ABSTRACT

The invention relates to a series of new compounds, to salts of these compounds and to methods for the preparation of the compounds. The new compounds have the general formula:

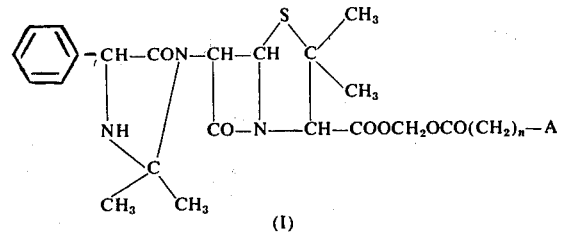

(I)

in which $n$ is an integer from 0 to 5; and A is selected from the group consisting of an unsubstituted or substituted aliphatic, alicyclic, aromatic and heterocyclic radical.

The compounds of the invention are broad-spectrum antibiotics especially usable for oral administration.

3 Claims, No Drawings

DERIVATIVES OF α-AMINOBENZYLPENICILLIN

This invention relates to a group a new derivatives of α-aminobenzylpenicillin, these derivatives having the formula

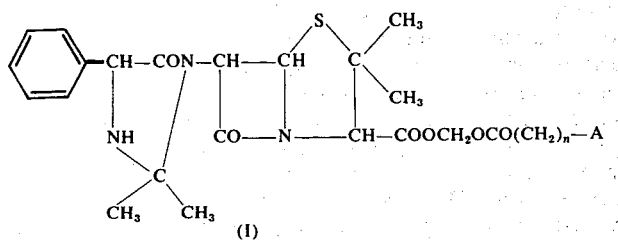

in which $n$ is an integer from 0 to 5; and A is an unsubstituted or substituted aliphatic, alicyclic, aromatic, or heterocyclic radical; to salts of these derivatives with pharmaceutically acceptable acids; and to methods of preparing these derivatives.

In particular, A may represent an aliphatic hydrocarbon radical in which the carbon chain can be straight or branched, saturated or unsaturated, having from 1 to 6 carbon atoms, such as methyl, ethyl, propyl, isopropyl, butyl, sec. and tert. butyl, pentyl, hexyl, and the like; an alicyclic, carbocyclic radical having from 3 to 10 carbon atoms as ring members and in which the ring or rings may be saturated or may contain one or two double bonds depending on the number of carbon atoms, such as cyclopentyl, cyclohexyl, 1-adamantyl, 1-bicyclo(2.2.2.) octyl, cyclopentenyl, cyclohexenyl, in which the double bond may be placed in the 2,3- or 3,4-position, and the like; an aromatic radical such as a monocyclic carbocyclic aryl radical, e.g. phenyl or a substituted phenyl radical, a bicyclic carbocyclic aryl radical, e.g. 1- or 2-naphthyl or substituted naphthyl radical; a heterocyclic aryl radical, which may contain from 5 to 10 atoms as ring members, such as pyridyl, pyrazinyl, pyrimidyl, thienyl, furyl, or quinolyl, in which the hetero atom may be in any of the available positions and which may further have substituents in one or more of the remaining positions. The radical A may as already mentioned have further substituents, such as lower alkyl, e.g. methyl, ethyl, propyl, isopropyl, butyl; lower alkoxy e.g. methoxy, ethoxy; lower alkylthio e.g. methylmercapto or ethylmercapto; halolower alkyl e.g. mono-, di- or trifluoromethyl, mono-, di- or trichloromethyl or the ethyl homologues and the corresponding bromo derivatives; halogens e.g. fluorine, bromine or chlorine; or nitro groups. The substituents may be placed in all possible positions.

It is known that the acid-resistant α-aminobenzylpenicillin is a broad-spectrum antibiotic with a widespread use. It is a disadvantage, however, that when orally administered, α-aminobenzylpenicillin is insufficiently absorbed in the organism, and it is one object of the present invention to provide new antibiotically active derivatives of α-aminobenzylpenicillin which, with a view to adequate absorption, distribution in the organism, and the like factors, are superior to α-aminobenzylpenicillin.

A derivative of α-aminobenzylpenicillin of the generic name hetacillin which stands for 6-(2,2-dimethyl-5-oxo-4-phenyl-1-imidazolidinyl)-penicillanic acid and of the formula II below

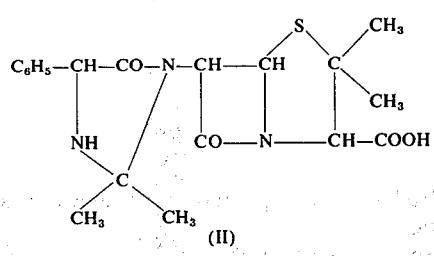

is known to be easily decomposed in the body fluid to α-aminobenzylpenicillin and according to known experiments described in Ann. N.Y. Acad. Sci. 145, 291–297, (1967) in possession of the property of producing serum levels of the same order as α-aminobenzylpenicillin after oral administration.

Esters of formula III

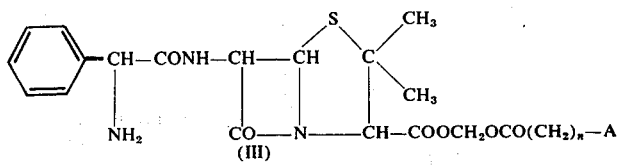

in which A and $n$ have the meanings hereinbefore defined are also known, (J.Med.Chem. 13, 607 (1970)), which when exposed to the influence of enzymes present in the body fluids or enzymes produced by microorganisms, e.g. pathogenic micro-organisms, are readily hydrolyzed to α-aminobenzylpenicillin. After oral administration of the esters of formula III very high serum levels of α-aminobenzylpenicillin are obtained, in fact serum levels which are substantially the same as those obtained after parenteral administration of α-aminobenzylpenicillin and thus they are superior from a therapeutical point of view. Their bitter taste, however, is a disadvantage which necessitates administration of the compounds of formula III in the form of capsules, special coated tablets or pills or similar forms of administration which are less usable in pediatric practice where a suspension is the preferred form of administration.

It has now been found that derivatives of formula I has a less pronounced bitter or unpleasant taste, whereas they are well-tolerated drugs suitable for suspensions for oral administration producing the above mentioned favourable high serum levels of free α-aminobenzylpenicillin after oral administration of dosages from 0.025 g. to 1 g. and preferably from 0.1 to 0.8 g. administered once or more times a day at appropriate intervals. Thus, a daily dose will preferably amount to from 1 to 3 g. of the compounds of the invention.

Such suspensions can for instance be made as aqueous suspensions, which besides the ester contain a suitable amount of sugar and/or sweeteners and preservatives and furthermore can contain stabilizers, such as carboxymethyl cellulose, and flavouring and colouring agents. Also oily suspensions can be prepared by suspending the compound in question and a sweetening agent in a vegetable oil, which can be stabilized with aluminum monostearate. Flavouring and colouring agents can also be added, if convenient.

It is another object of the present invention to provide methods for the preparation of the new derivatives of formula I.

One method comprises the reaction of a compound of formula II or an alkali metal salt or tertiary ammonium salt thereof with a compound of formula IV according to the reaction scheme:

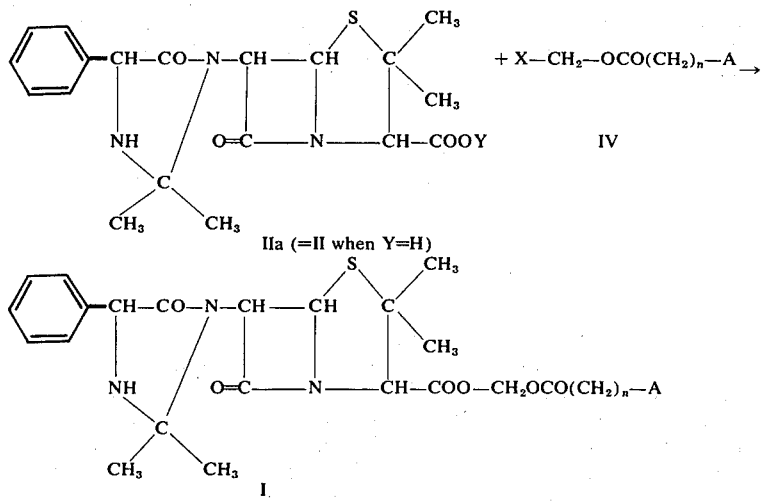

in which formulae $n$ and A are defined hereinbefore, Y is hydrogen or an alkali metal or a tert. ammonium group, and X is a halogen atom, preferably chlorine or bromine, or an alkylsulphonyloxy or an arylsulphonyloxy radical.

Some of the starting compounds of formula Iv are known compounds the preparation of which is described in the literature. Others are new, but can be prepared in the same way as the known compounds, using methods which are standard procedures for this type of compounds.

Among such methods may be mentioned the reaction of an acid halide with paraformaldehyde (as described in e.g. J.A.C.S. 43, 660 (1921)) or the halogenation of methyl esters (as described in e.g. Acta Chem. Scand. 20, 1273 (1966) and references cited there).

The reaction of the compound of formula IIa with the compounds of formula IV can be performed at or below room temperature or by gently heating up to the boiling point of the solvent depending on the meaning of Y and X. Different organic solvents or mixtures thereof with water may be used, for example, acetone, dioxane, tetrahydrofuran, methylene chloride and dimethylformamide. The reaction products are crystalline or oily products. By repeated precipitations the oily products can be obtained as crystalline or amorphous powders.

Another suitable method for the preparation of compounds of formula I comprises the reaction of a derivative of α-aminophenylacetic acid of formula V with an ester of 6-aminopenicillanic acid of formula VI.

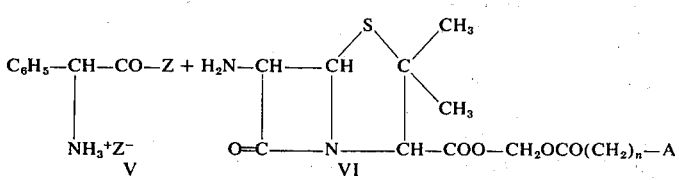

in which formulae A and $n$ have the meanings hereinbefore defined and Z stands for halogen, in the presence of an excess of acetone, the reaction being performed over a period of time sufficient to accomplish a major degree of acylation whereafter the reaction is finished by successively adjusting the pH to a value between 5.5 to 9.5 whereby the desired compound of formula I is directly obtained.

In a particular suitable method a compound of formula I is obtained from a starting substance of formula II or an alkali metal salt or a tertiary ammonium salt thereof, which in a first step is reacted with a compound of the formula:

$R_1CH_2R_2$   VII wherein $R_1$ stands for halogen, and $R_2$ for halogen, an alkylsulfonyloxy or an arylsulphonyloxy radical or a corresponding reactive radical, whereby is formed a hetacillin halomethyl ester of the formula:

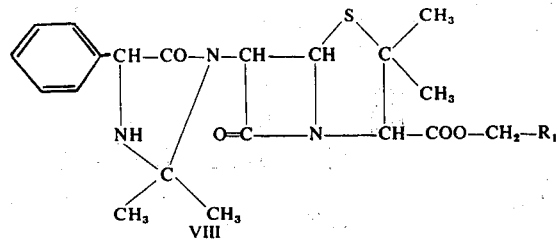

in which $R_1$ has the meaning defined above, and in a second step the compound of formula VIII thus obtained reacted with a salt of an acid of the formula

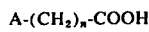

A-(CH$_2$)$_n$-COOH     IX in which A and $n$ have the meaning hereinbefore defined, to form the desired compound of formula I.

The hetacillin halomethyl esters of formula VIII are new compounds which also form part of this invention.

The invention will now be illustrated by the following non-limiting Examples:

EXAMPLE 1

Pivaloyloxymethyl 6-(2,2-dimethyl-5-oxo-4-phenyl-1-imidazolidinyl)-penicillanate.

To a suspension of hetacillin (974 mg.) in dimethylformamide (10 ml.) is added triethylamine (0.39 ml.) and, after stirring for 10 minutes, chloromethyl pivalate (0.75 ml.). The mixture is stirred for 20 hours at room temperature. After dilution with ethyl acetate (40 ml.), the mixture is washed with water (4 × 10 ml.) and the organic phase dried and evaporated in vacuo to yield the crude ester as a yellowish oil. Dry column chromatography of this material (adsorbent: Silicic acid, Mallinckrodt, 100 mesh. Eluent: Cyclohexane - ethyl acetate 4:6) affords pure hetacillin pivaloyloxymethyl ester as a colourless amorphous powder.

The IR-spectrum (KBr) shows bands at 1790 ($\beta$-lactam carbonyl), 1760 (ester carbonyl) and 1705 ($\gamma$-lactam carbonyl) cm$^{-1}$, The NMR-spectrum (CDCl$_3$) shows signals at $\delta$ = 1.23 (s, 9 H, C)CH$_3$)$_3$), 1.47 and 1.71 (2 s, 6 H, C(CH$_3$)$_2$), 1.54 (s, 6 H, C)CH$_3$)$_2$) 2.16 (s, 1 H, NH), 4.59 (s, 1 H,CH-3), 4.70 (s, 1 H, C$_6$H$_5$CH), 4.78 and 5.60 (2 d, J = 4 cps, 2 H, CH-5 and CH-6 ), 5.84 (AB$_q$, 2 H, OCH$_2$O), and 7.39 (m, 5 H, aromatic CH) ppm. Tetramethylsilane is used as internal reference.

EXAMPLE 2

Acetoxymethyl 6-(2,2-dimethyl-5-oxo-4-phenyl-1-imidazolidinyl)-penicillanate.

To a suspension of sodium D-$\alpha$-aminobenzylpenicillinate (2.0 g.) and potassium bicarbonate (0.5 g.) in acetone (20 ml.), bromomethyl acetate (1.0 ml.) is added and the mixture stirred for 16 hours at room temperature. After dilution with ethyl acetate (80 ml.), the mixture is washed with water (3 × 10 ml.) and the organic layer dried and evaporated in vacuo. The residual oil is washed repeatedly by decantation with petroleum ether to remove excess of bromomethyl acetate. The yellowish gum thus obtained is dissolved in ethyl acetate - ether 1:1 (60 ml.), water (40 ml.) is added and the apparent pH value of the mixture adjusted to 2.5 by addition of 1 N hydrochloric acid while stirring. The organic phase is separated, washed with water (2 × 10 ml.), dried, and evaporated in vacuo. Dry column chromatography of the residual gum in the same way as described in Example 1 affords pure hetacillin acetoxymethyl ester as a slightly yellowish gum.

EXAMPLE 3

Chloromethyl 6-(2,2-dimethyl-5-oxo-4-phenyl-1-imidazolidinyl)-penicillinate.

To a solution of hetacillin (3.9 g.) and triethylamin (1.54 ml.) in dimethylformamide (30 ml.), chloroiodomethane (3.7 ml.) is added and the mixture stirred for 8 hours. After addition of ethyl acetate (120 ml.), the mixture is washed with water (4 × 30 ml.). The organic layer is dried and evaporated in vacuo to yield crude hetacillin chloromethyl ester as a yellowish gum. This product can be used for the next step without further purification.

Dry column chromatography of a sample of the crude ester (Adsorbent: Silicic acid, Mallinckrodt, 100 mesh. solvent system: Cyclohexane-ethyl acetate 3:7) affords pure hetacillin chloromethyl ester as colourless oil.

EXAMPLE 4

Pivaloyloxymethyl 6-(2,2-dimethyl-5-oxo-4-phenyl-1-imidazolidinyl)-penicillanate.

To a solution of hetacillin chloromethyl ester (438 mg.) in dimethylformamide (5 ml.), sodium pivalate, dihydrate (176 mg.) is added and the mixture stirred for 24 hours at room temperature. After dilution with ethyl acetate (25 ml.), the mixture is washed with water (4 × 5 ml.), dried and evaporated in vacuo. Dry column chromatography of the residual oil on silicic acid (Eluent: Cyclohexane-ethyl acetate 4:6) affords the desired compound as an amorphous powder. The NMR-spectrum and TLC-data prove the identity with the compound described in Example 1.

What we claim is:

1. Hetacillin chloromethyl esters of the formula

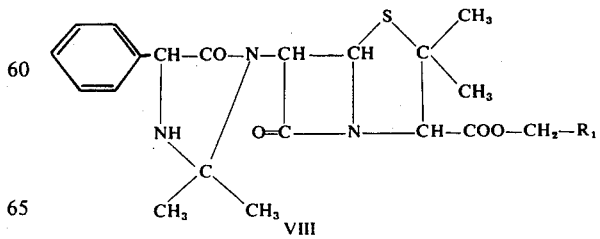

in which $R_1$ stands for chlorine.

2. A compound constituting the pivaloyloxymethyl ester of hetacillin having the formula
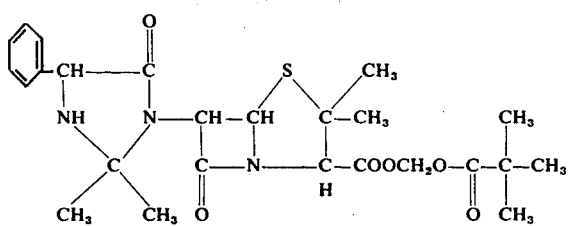
3. A compound selected from the group consisting of the pivaloyloxymethyl ester of hetacillin having the formula
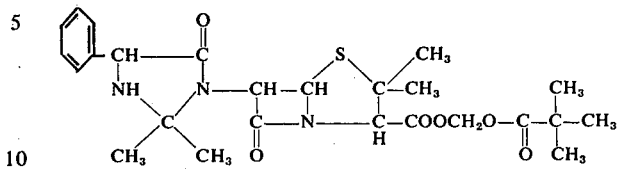
and the pharmaceutically acceptable non-toxic salts thereof.
* * * * *